United States Patent
Nakada (10) Patent No.: US 7,543,938 B2
(45) Date of Patent: Jun. 9, 2009

(54) METHODS AND DEVICES FOR PREVENTION AND TREATMENT OF MYOPIA AND FATIGUE

(76) Inventor: Tsutomu Nakada, 1200 California Ave., #7A, San Francisco, CA (US) 94109

( * ) Notice: Subject to any disclaimer, the term of this patent is extended or adjusted under 35 U.S.C. 154(b) by 68 days.

(21) Appl. No.: 11/856,216

(22) Filed: Sep. 17, 2007

(65) Prior Publication Data

US 2009/0073375 A1  Mar. 19, 2009

(51) Int. Cl.
*A61B 3/00* (2006.01)
(52) U.S. Cl. .................................. 351/203; 351/200
(58) Field of Classification Search .......... 351/200–204
See application file for complete search history.

(56) References Cited

U.S. PATENT DOCUMENTS

| | | | |
|---|---|---|---|
| 3,883,225 A | | 5/1975 | Rehm |
| 4,848,899 A | | 7/1989 | Kobayashi et al. |
| 5,051,931 A | | 9/1991 | Cheu et al. |
| 5,173,724 A | * | 12/1992 | Bonham et al. ............. 351/203 |
| 5,204,702 A | | 4/1993 | Shapiro |
| 6,347,869 B1 | | 2/2002 | Xu et al. |
| 6,709,101 B1 | | 3/2004 | Lee |
| 2003/0208189 A1 | | 11/2003 | Payman |
| 2005/0002083 A1 | | 1/2005 | Fergason |
| 2005/0213035 A1 | | 9/2005 | Yoshimeki et al. |
| 2006/0028489 A1 | * | 2/2006 | Uyttendaele et al. ........ 345/646 |

FOREIGN PATENT DOCUMENTS

EP  0 362 692  4/1990

* cited by examiner

*Primary Examiner*—Huy K Mai
(74) *Attorney, Agent, or Firm*—Townsend and Townsend and Crew LLP (57) ABSTRACT

An electronic image shown on a display can be shifted to the left for left eye viewing and shifted to the right for right eye viewing. A left eye shutter can be positioned over the left eye and a right eye shutter positioned over the right eye. The left eye shutter can open when the image shown on the display is shifted to the left, and the right eye shutter can open when the image shown on the display is shifted to the right, such that each eye can view the image without substantial convergence. In addition to relieving convergence, embodiments of the present invention may relieve prolonged ciliary muscle spasms that can result in pseudomyopia, and may also decrease the onset and severity of myopia, for example developmental myopia.

34 Claims, 9 Drawing Sheets

METHODS AND DEVICES FOR PREVENTION AND TREATMENT OF MYOPIA AND FATIGUE

CROSS-REFERENCES TO RELATED APPLICATIONS

NOT APPLICABLE

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

1. Field of the Invention

The present invention is generally directed to the relief of eye convergence. Embodiments of the present invention provide methods and devices for the prevention and treatment of myopia due to prolonged use of computer displays, computer games and television. Although specific reference is made to the relief of eye convergence with an electronic image on a display screen, embodiments of the present invention can be used with other images and other displays.

Displays are present in many places and used in a wide variety of applications. For example, displays are used with computers, video games, home movie theaters, telephones and televisions. In many instances, it can be desirable to have a display positioned in proximity to the user. Proximity of the display to the user can allow the images shown on the display to appear larger to the user, for example with a computer and video displays which are often about one meter or less from the user.

Although placing a display near a user can have advantages, there can also be disadvantages that may not be fully corrected in many situations. Many people who can accommodate with the lens of the eye are able look at a nearby display easily as the lens of the eye can accommodate to bring the display into focus. However, prolonged accommodation of the eye can result in functional myopia, or nearsightedness. Since an accommodation reflex occurs when one sees near objects (so called, near response or accommodation response), it can be difficult, and in some instances virtually impossible, to avoid contraction of ciliary muscles as far as one focuses on near objects including computer display, computer games, and television.

Work in relation to embodiments of the present invention suggest that prolonged use of computer displays, computer games and television may result in myopia. For example, prolonged viewing of a nearby display may result in ciliary muscle spasms that result can in functional myopia such that the user may be nearsighted while the spasm persist, even while viewing a distant object. In addition, prolonged viewing of a nearby display and associated ciliary muscle spasm may play a role the development permanent myopia, for example developmental myopia with adolescents.

In light of the above, it would be desirable to provide improved methods and/or apparatus for viewing objects, such as displays, that avoid at least some of the above mentioned disadvantages.

2. Description of the Background Art

Patents and patent publications that may be relevant include U.S. Pat. Nos. 6,709,101; 6,347,869; 5,204,702; 3,883,225; U.S. Pat. App. Pub. No. 2005/0213035; and EP 0362692.

BRIEF SUMMARY OF THE INVENTION

The present invention is generally directed to relief of eye convergence, and more specifically to eye strain associated with display devices. Embodiments of the present invention provide methods and devices for the prevention and treatment of myopia due to prolonged use of computer displays, computer games and television. Although specific reference is made to an electronic image on a display, embodiments of the present invention can be used with other images and other displays. In some embodiments, the electronic image shown on the display is shifted to the left for left eye viewing and shifted to the right for right eye viewing. A left eye shutter can be positioned over the left eye and a right eye shutter positioned over the right eye. The left eye shutter can open when the image shown on the display is shifted to the left, and the right eye shutter can open when the image shown on the display is shifted to the right, such that each eye can view the image without substantial convergence. In addition to relieving convergence, embodiments of the present invention may relieve, or at least decrease, prolonged ciliary muscle spasms that can result in pseudomyopia. Thus, in addition to decreasing eye convergence and associated eye strain and fatigue, some embodiments of the present invention may also decrease the onset and severity of myopia, for example developmental myopia.

In a first aspect, embodiments of the present invention provide a method for relieving eye convergence while viewing an electronic image on a display, such as a projection display, computer screen or video game screen. The electronic image is shifted horizontally on the display according to a time pattern, for example a video frame rate. Left eye and right eye viewing of the display is alternated according to the time pattern. The distance is sufficient for each eye to view the image without substantial convergence.

In many embodiments, the time pattern is invariant. In specific embodiments, the images shift at a rate, and the rate is in the range from 30 Hz to 120 Hz. In specific embodiments, the preselected distance comprises a range, and the range from 0.1 cm to 5 cm.

In many embodiments, left eye and right eye vision is alternated by alternately opening and shutting a shutter worn over each eye. In some embodiments, liquid crystal shutters can be energized and de-energized to open and shut the shutter worn over each eye. In some embodiments, mechanical shutters may be opened and shut to open and close the shutter worn over each eye.

In many embodiments, the image shift distance comprises a preselected distance, for example a default distance. In some embodiments, the image shift distance may correspond to a distance selected by the user. For example, the selected distance can be perceived by the user and selected in response to user comfort. In specific embodiments, the image shift distance can be incrementally increased to a maximum distance for which the user perceives the image as a single image. Thus, although a range of distances can provide relief, the maximum distance can be selected in response to user perception.

In many embodiments, the image is shifted to the left when viewed with left eye of the user and the image is shifted to the right when viewed with a right eye of the user. A magnification of the image may be decreased by and amount for viewing with each eye, and the amount of decrease in magnification of the image can be the same for both eyes. A magnification of the image can be decreased for viewing with each eye such that a size of the image on the display is reduced and the image is not cropped when shifted for viewing with each eye on the display.

In another aspect, a system for relieving eye convergence while viewing an electronic image on a display is provided. The system comprises electronic circuitry for receiving an electronic image and generating an output comprising a series of frames of the image. The frames are alternately right shifted and left shifted by a preselected distance according to a time pattern. The distance is sufficient for each eye to view the image without substantial convergence. The left and right eye shutters are configured to alternately open and close according to the time pattern.

In many embodiments, a display is connected to receive the output of the electronic circuitry. A source can be connected to feed the electronic image to the electronic circuitry.

In many embodiments, the electronic circuitry produces a timing signal which is coupled to the left and right shutters. The timing signal can be coupled by a wire. In some embodiments, the timing signal is wirelessly coupled from the electronic circuitry to the left and right shutters.

In many embodiments, the time pattern is invariant. The images can shift at a rate, and the rate is in the range from 30 Hz to 120 Hz. The preselected distance may be in a range from 0.1 cm to 5 cm.

In many embodiments, the preselected distance is user selectable with an input, and the electronic circuitry is configured to adjust the preselected distance in response to the input. In some embodiments, the electronic circuitry can be configured to display the alternately right shifted and left shifted frames on the display such that the user can select the distance. In specific embodiments, the electronic circuitry is configured to increase incrementally the distance to a maximum distance at which the user perceives the image as a single image.

In many embodiments, the electronic circuitry is configured to open and shut a shutter worn over each eye so as to alternate left eye and right eye vision. In some embodiments, the left eye and right eye shutters comprise liquid crystal shutters configured to open and close in response to a timing signal. In some embodiments, the left eye and right eye shutters comprise mechanical shutters configured to open and close in response to a timing signal.

In many embodiments, the system comprises a frame configured to be worn by a user, and the left and right eye shutters are mounted on the frame. In some embodiments, the system comprises a left lens and a right lens, and each lens is connected to the frame to correct vision of the user.

In many embodiments, the frames and shutters are configured for use with lenses that correct vision of the user. The lenses may correct at least one of a nearsightedness, a farsightedness, an astigmatism or a pseudomyopia of the user. In specific embodiments, the lenses comprise reading glasses.

DETAILED DESCRIPTION OF THE INVENTION

Embodiments of present invention can provide relief of eye convergence and eye strain associated with display devices. Although specific reference is made to an electronic image on a display, embodiments of the present invention can be used with other images and other displays. In some embodiments, the electronic image shown on the display, for example on a display screen, is shifted to the left for left eye viewing and shifted to the right for right eye viewing. A left eye shutter can be positioned over the left eye and a right eye shutter positioned over the right eye. The left eye shutter can open when the image shown on the display is shifted to the left, and the right eye shutter can open when the image shown on the display is shifted to the right, such that each eye can view the image without substantial convergence. In addition to relieving convergence, embodiments of the present invention may relieve, or at least decrease, prolonged ciliary muscle spasms that can result in pseudomyopia. Thus, in addition to decreasing eye convergence and associated eye strain and fatigue, some embodiments of the present invention may also decrease the onset and severity of myopia, for example developmental myopia.

Embodiments of the present invention provide decreased near vision response with targets that are near the patient. The near vision response comprises a triple response, or triad, in which a person's eyes converge, the lenses of both eyes accommodate, and the pupils of both eyes constrict. The triad shown below is made with reference to an emmetropic eye, according to some embodiments of the present invention. Eyes with optical correction can act in a similar manner to the emmetropic eye shown, for example eyes with spectacles, contact lenses and eye with surgical correction of refractive error. Also, eyes with some refractive error can respond to a near vision stimulus in a manner similar to the emmetropic eye, according to embodiments of the present invention.

Figure 1A:
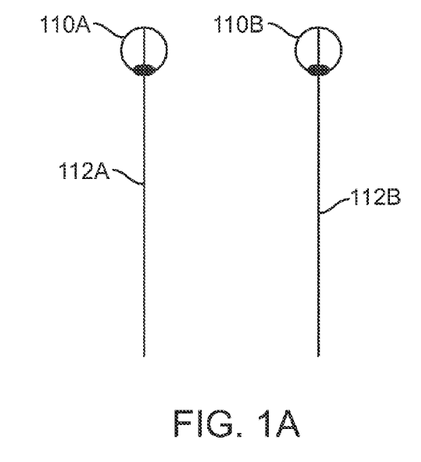
FIG. 1A shows binocular viewing of a distant target.

FIG. 1A shows binocular viewing of a distant target. A first eye, or right eye 110A, and a second eye, or left eye 110B, of are shown in a parallel arrangement. A line of sight 112A from eye 110A to the distant target is parallel to a line of sight 112B from eye 110B to the target. Such binocular viewing of a distant target is associated with a relaxed state of the eye 110A and eye 110B.

Figure 1B:
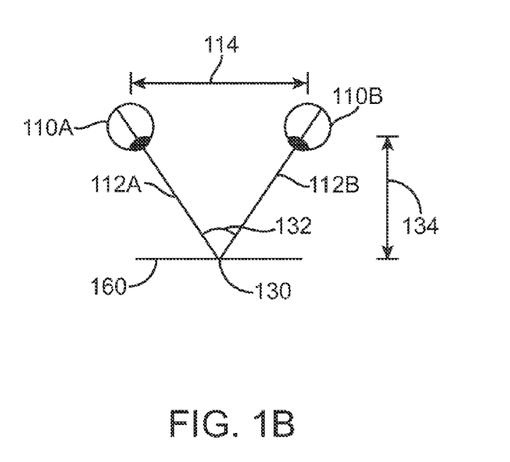
FIG. 1B shows binocular convergence in response to a near target.

FIG. 1B shows binocular convergence in response to a near target 130. Right eye 110A and left eye 110B are fixated on near target 130, such that line of sight 112A and line of sight 112B are intersect target 130 at an angle 132. Near target 130 can be located on a display 160. Right eye 110A and left eye 110B are separated by an interpupillary distance 114, or IPD. Righteye 110A and left eye 110B are separated from display 160 by an object distance 134.

Figure 1C:
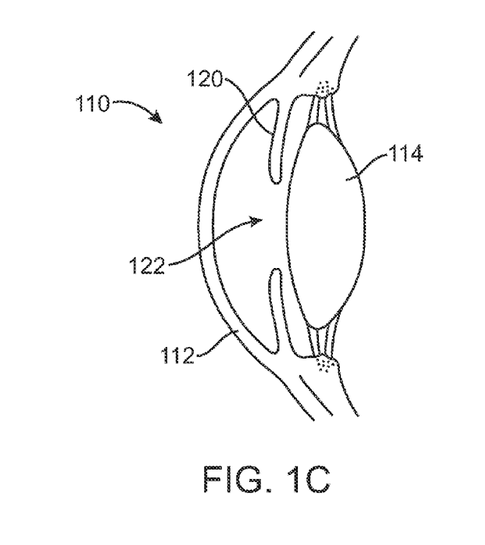
FIG. 1C shows a lens of an eye in a relaxed state, in response to a distant target as in FIG. 1A.

FIG. 1C shows an anterior segment of an eye 110 in a relaxed state, in response to a distant target as in FIG. 1A. Eye 110 includes a cornea 112, an iris 120 and a lens 114. Iris 120 defines a pupil 122 through which light passes so as to be refracted by lens 114. As cornea 112 comprises a curved surface, cornea 112 and lens 114 provide optical power and refract light to form an image of target 130 on the retina. Eye 110 includes a ciliary muscle 116. In the relaxed state of accommodation, ciliary muscle 116 is relaxed.

Figure 1D:
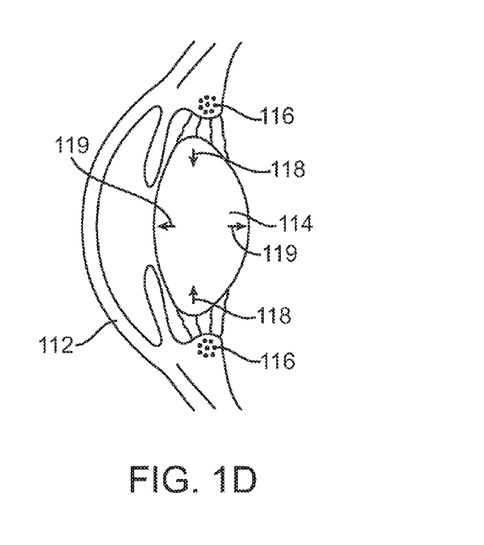
FIG. 1D shows accommodation of the lens of the eye in response to the near target as in FIG. 1B.

FIG. 1D shows accommodation of the eye as in FIG. 1C in response to the near target as in FIG. 1B. Ciliary muscle 116 constricts in response to near target 130 and changes lens 114 so as to provide an adjustment to the focus of the image of the target formed on the retina. Constriction of ciliary muscle 116 moves the outer periphery of lens 114 inward as shown by arrows 118. The anterior surface of lens 114 moves forward and the posterior surface of lens 114 moves posteriorly, as shown by arrows 119. Consequently, lens 114 is thicker with increased curvature to increase the optical power of lens 114 and ensure that the near target is properly focused on the retina.

Figure 1E:
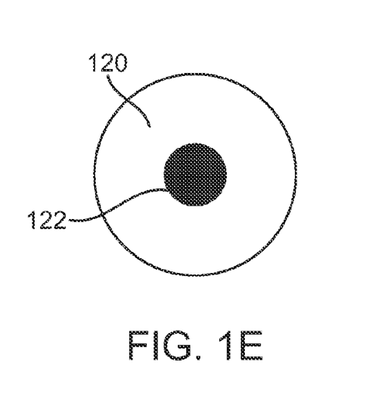
FIG. 1E shows a pupil associated with a relaxed state of the eye as in FIG. 1C.

FIG. 1E shows a pupil 122 associated with a relaxed state of the eye as in FIG. 1C. Pupil 122 is defined by iris 120 as described above.

Figure 1F:
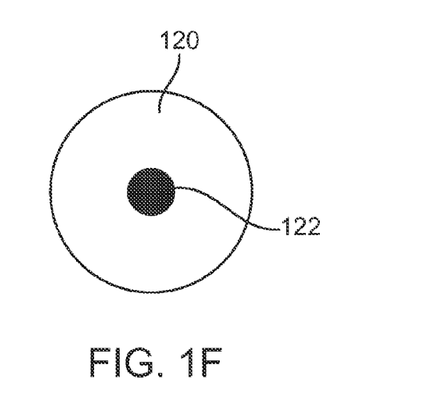
FIG. 1F shows pupillary constriction of the eye as in FIG. 1D.

FIG. 1F shows pupillary constriction pupil 122 of eye 110 in an accommodative state as in FIG. 1D. Pupil 122 is smaller and constricted to compensate for the structural changes of lens 114. Work in relation with embodiments of the present invention suggests that pupillary constriction may restrict the light passage to ensure proper usage of thickened lens.

Figure 1G:
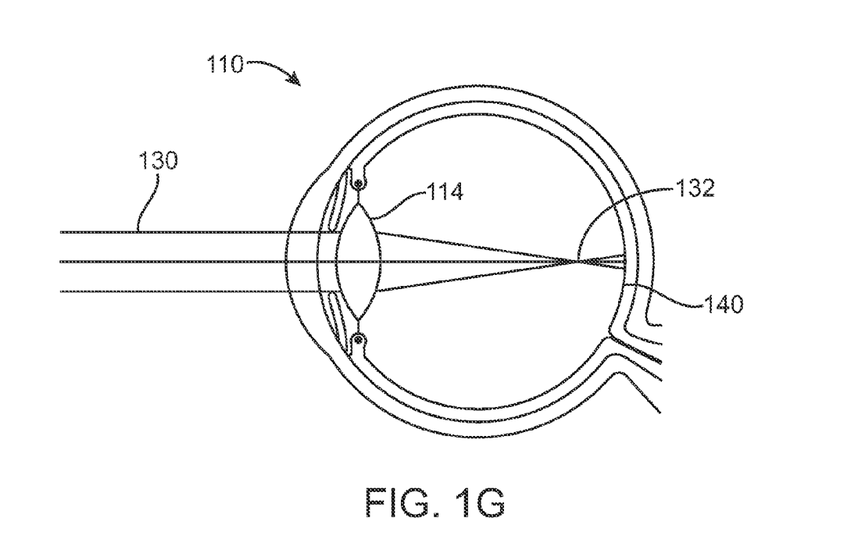
FIG. 1G shows pseudomyopia that can result from a prolonged response to the near target as in FIG. 1B.

FIG. 1G shows pseudomyopia that can result from a prolonged response to the near target as in FIG. 1B. Prolonged near response may produce ciliary muscle spasms, resulting in pseudomyopia, or functional pseudomyopia. Light rays 130 are shown in a parallel arrangement entering eye 114 from a distant target. Eye 114 comprises a retina 140. Lens 114 remains in an accommodative state with pupillary constriction, as described above. Consequently, light rays 130 come to a focus 132, or circle of least confusion, in front of retina 140, consistent with myopia. Work in relation to embodiments of the present invention suggests that pseudomyopia can be decreased, or even eliminated, by shifting the position of the object seen by each eye such that the object appears distant to the user.

Figure 1H:
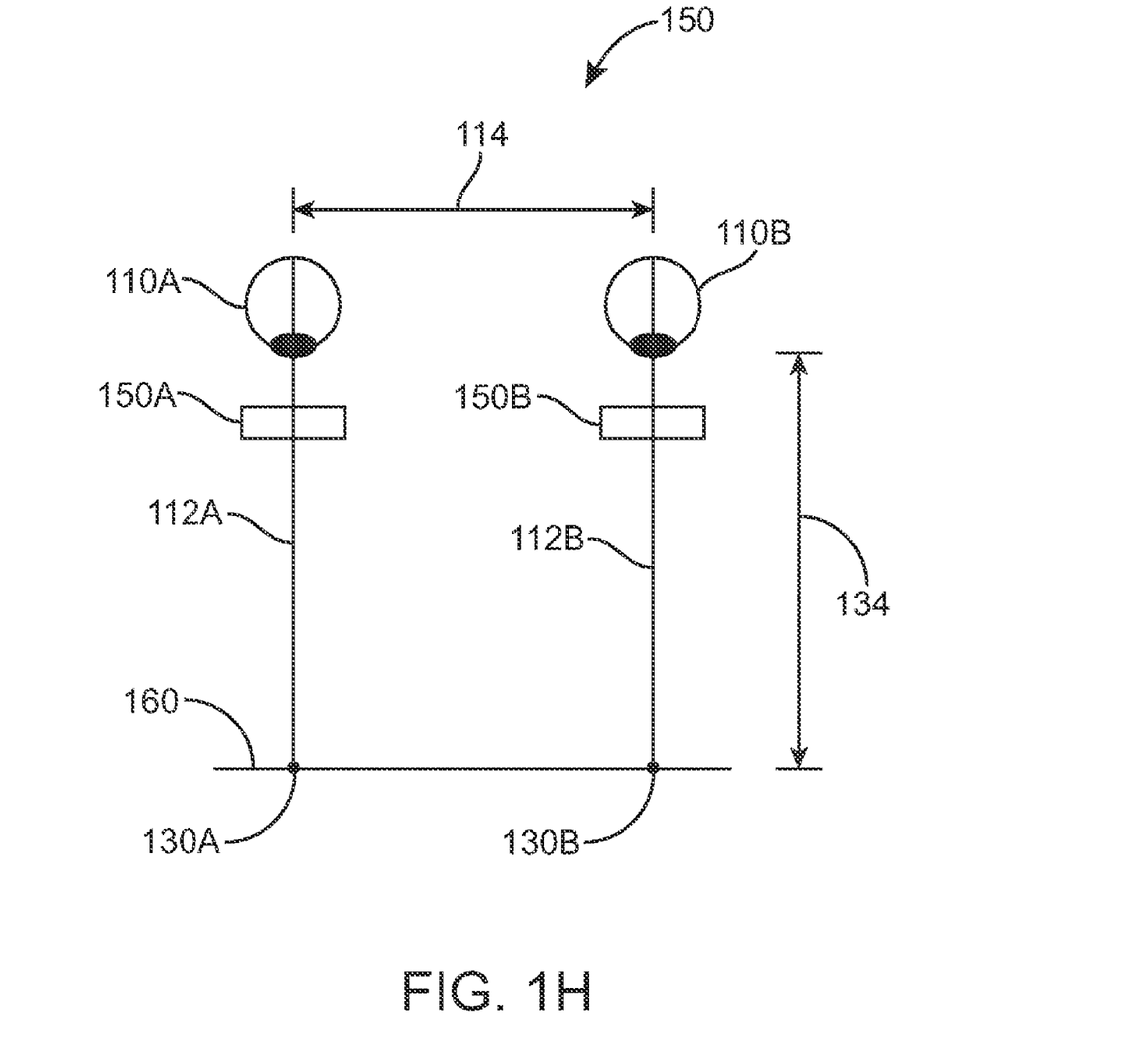
FIG. 1H shows a schematic illustration of a system to inhibit accommodation in response to a near stimulus, according to embodiments of the present invention.

FIG. 1H shows a schematic illustration of a system 150 to inhibit accommodation in response to a near stimulus. System 150 includes a right shutter 150A placed in front of right eye 110A of the user, and a left shutter 110B placed in front of the left eye 110B. A display 160 comprises a screen that shows a left near target 130A and a right near target 130B. Display 160 alternatively shows right near target 130A and left near target 130B. Right shutter 150A is open when right near target 130A is shown on display 160, and left shutter 150B is open when left near target 130B is shown on display 160. Although reference is made to near target 130, right near target 130A and left near target 130B by way of example, system 150 can work with many visual stimuli including video frames, video images, computer generated video and images, letters characters and the like. Right eye 110A and left eye 110B are separated by interpupillary distance 114. In many embodiments, the information contained in each of right near target 130A and left near target 130B can be substantially similar, for example identical. In many embodiments, each near target may be shifted by a maximum distance that the subject can subjectively see, or perceive and comfortably see a single target. Left eye 110A and left eye 110B are separated from the screen by object distance 134, for example 0.5 meters. In some embodiments, near vision correction may also be provided, for example +2D of correction, such that the target can be brought into focus on the retina without strong accommodation.

Figure 2A:
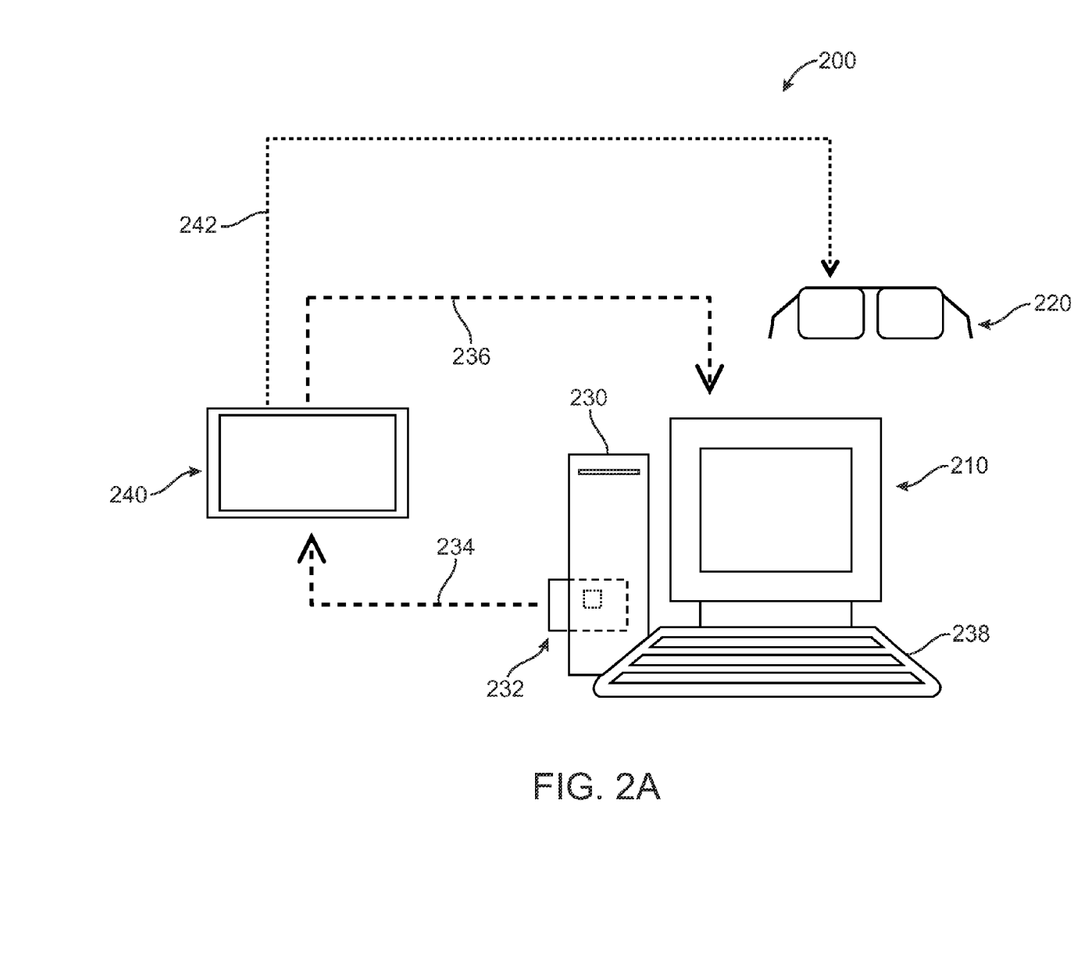
FIG. 2A shows a system to prevent and treat myopia and fatigue, according to embodiments of the present invention.

FIG. 2A shows a system 200 to prevent and treat myopia and fatigue, according to embodiments of the present invention. System 200 includes a display 210. Display 210 may comprise a liquid crystal display (LCD), a cathode ray tube (CRT) monitor, a digital light processing (DLP) display, a digital micro-mirror display, a high definition television (HDTV) display, and many known displays that can be connected to computers, televisions and video games and digital move cameras. System 200 includes glasses 220 for viewing display 220. Glasses 220 can include shutters, for example liquid crystal (LC) shutters, which open and close in synchronization with frames of display 210, such that images shown on the display appear distant to the user. System 200 may include a processor 230, for example a personal computer (PC) with video circuitry, for example a video card 232. Video card 232 may comprise an on board video processing chip, or processor, with digital video interface (DVI) and/or video graphics array/adaptor (VGA) output. Processor 230 comprises an input device 238 which may comprises a keyboard, keypad, touch screen, mouse, trackball, laser pointer, voice activated user control, joy stick, steering wheel, and many known user interface input devices. In some embodiments, the user can use the input device 238 to adjust the shift of the left and right eye images shown on the display. System 200 includes electronic shift circuitry 240 for shifting frames. A cable 234 may connect video card 232 with electronic shift circuitry 240. Electronic shift circuitry receives as input a video source, for example original frame images, or frames, from video card 232 via cable 234. Electronic shift circuitry 240 transmits a synchronization signal 242 to shutter glasses 220. Electronic shift circuitry 240 transmits processed frames to display 210 over a cable 236.

Figure 2B:
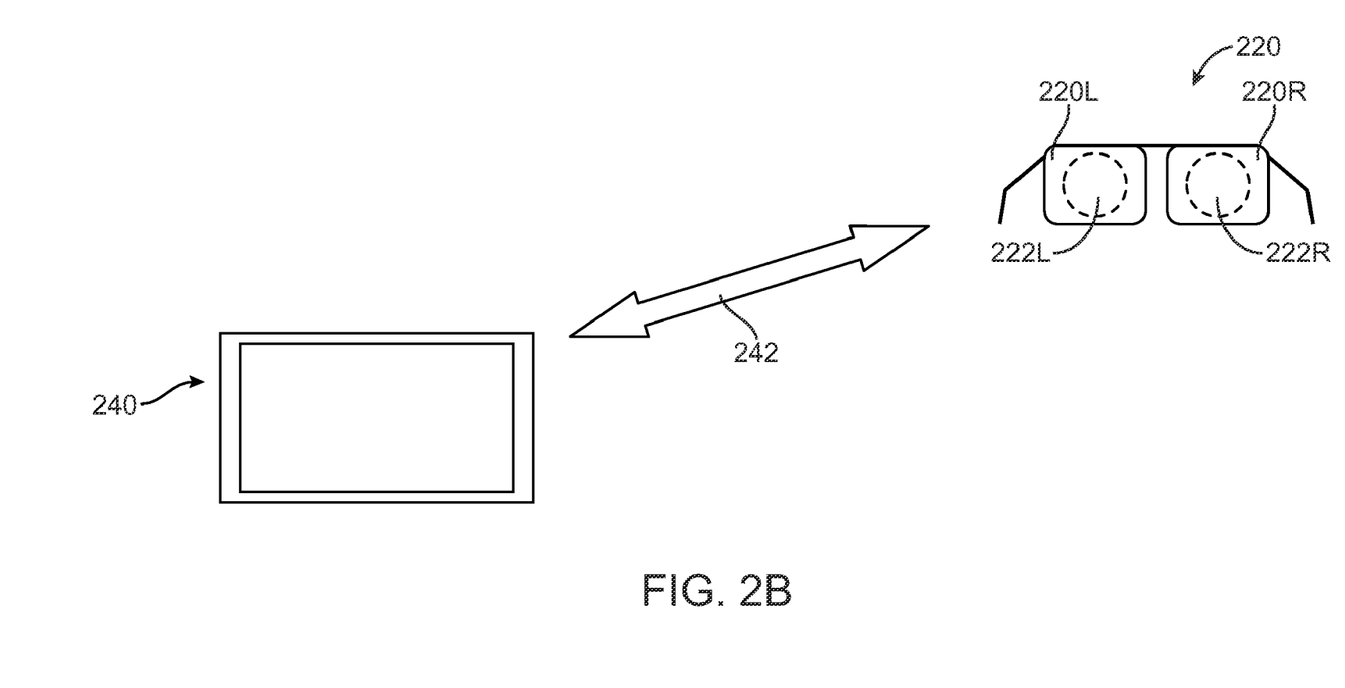
FIG. 2B shows synchronization between the shift device and shutter glasses of the system shown in FIG. 2A.

FIG. 2B shows synchronization signal 242 transmitted from electronic shift circuitry 240 to shutter glasses 220 of the system shown in FIG. 2A. Synchronization signal 242 can be transmitted over a wire, e.g. wired synchronization, or wirelessly, e.g. wireless synchronization. Synchronization signal 242 can include both radiofrequency (RF) and infrared (IR) signals.

Shutter glasses 220 may include a left shutter 220L and a right shutter 220R. Left shutter 220L and right shutter 220R may comprise known commercially available optical shutters, for example liquid crystal shutters, micro mirror shutters, and mechanical shutters. In some embodiments, shutter glasses 220 comprise known commercially available LC shutter glasses. Shutter glasses 220 may include a left lens 222L and a right lens 222R. Each of left lens 222L and right lens 222R can comprise at least one of a prescription lens to correct refractive error of the eye, a reading lens to provide near vision correction of the eye, or a sun glass lens. In some embodiments, each of left lens 222L and right lens 222L may comprise an individual lens that can be attached to shutter glasses 220. In some embodiments, shutter glasses 220 can be attached and/or combined with other glasses that are worn by the user, for example prescription glasses with near vision correction such as progressive addition lenses, bifocals and the like. The lenses may correct at least one of a nearsightedness, a farsightedness, an astigmatism or a presbyopia of the user. In specific embodiments, the lenses comprise reading glasses.

Shutter glasses 220 may comprise a frame configured to be worn by a user. The left and right eye shutters can be mounted on the frame. The left lens 222L and right lens 222R can each lens be connected to the frame to correct vision of the user. In many embodiments, the frames and shutters are configured for use with lenses that correct vision of the user, for example eyeglasses that can be worn with shutter glasses 220 as described above.

Electronic shift circuitry 240 can be designed in many ways. In some embodiments, shift circuitry 240 comprises an add on device, for example a box, that is plugged in between cable 234 and cable 236. In some embodiments, shift circuitry 240 comprises a video card that can be added to the computer. In some embodiments, electronic shift circuitry comprises an additional chip that can be added onto a video card. In some embodiments, electronic shift circuitry 240 may comprise a known video processor circuitry upgraded with software that configures the video processor circuitry to shift the images, for example video processors and circuits commercially available from nVidea of Santa Clara, Calif.

Figure 2C:
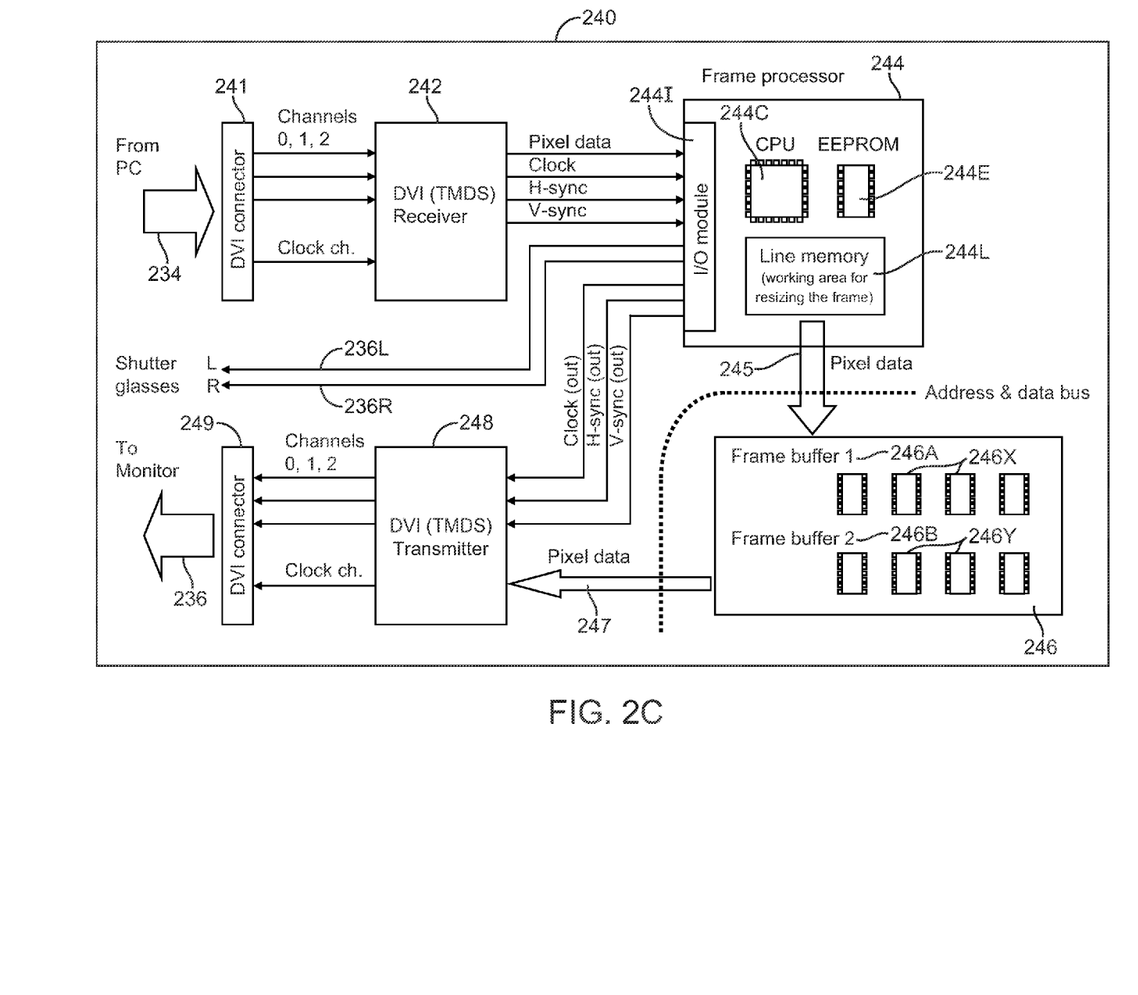
FIG. 2C shows detail of the shift device of the system shown in FIG. 2A.

FIG. 2C shows detail of the shift device of the system shown in FIG. 2A. A cable 234 provides video data from the video card. Cable 234 can be connected to a DVI connector 241. DVI connector 241 is connected to a DVI receiver 242, for example a commercially available transition minimized differential signaling (TDMS) receiver from Silicon Imaging Inc. of Costa Mesa, Calif. DVI receiver 242 may comprise a commodity IC. DVI receiver 242 is connected to an I/O module 244I of a frame processor 244. Frame processor 244 comprises a central processing unit or CPU 244C, an Electrically Erasable Programmable Read-Only Memory or EEPROM 244E, and a line memory 244L. EEPROM 244E can include instructions for CPU 244C, for example a frame processing program, that can be modified and upgraded. Electronic shift circuitry 240 comprises an Frame processor 244 that outputs pixel data 245 to a dual port video memory and controller 246. Controller 246 comprises a first frame buffer 246A and a second frame buffer 246B. First frame buffer 246A comprises processed frames 246X stored thereon, and second frame buffer 246B comprises processed frames 246Y stored thereon. Controller 246 reads out first frame buffer 246A and second frame buffer 246B as pixel data 247. Pixel data 247 is sent from controller 246 to a DVI transmitter 248, for example a commercially available TDMS transmitter from Silicon Imaging Inc. DVI transmitter 248 may comprise a commodity IC. DVI transmitter 248 is connected to DVI connector 249. DVI connector 249 is connected to cable 236, such that shifted frames are transmitted to display 210.

Shutter glasses 220 connected to timing signals from electronic shift circuitry 240. A left signal 236L is transmitted to the left shutter 220L, and a right signal 236R is transmitted to the right shutter. In some embodiments, the left and right shutter command signal may be multiplexed with single signal from the electronic shift circuitry 240. The signal from the electronic shift circuitry to the shutters synchronizes the viewing of each eye with the video frame presented on the display, such that the left shutter is open when the left eye image is on the display and the right eye shutter is open when the right eye image is on the display.

Figure 2D:
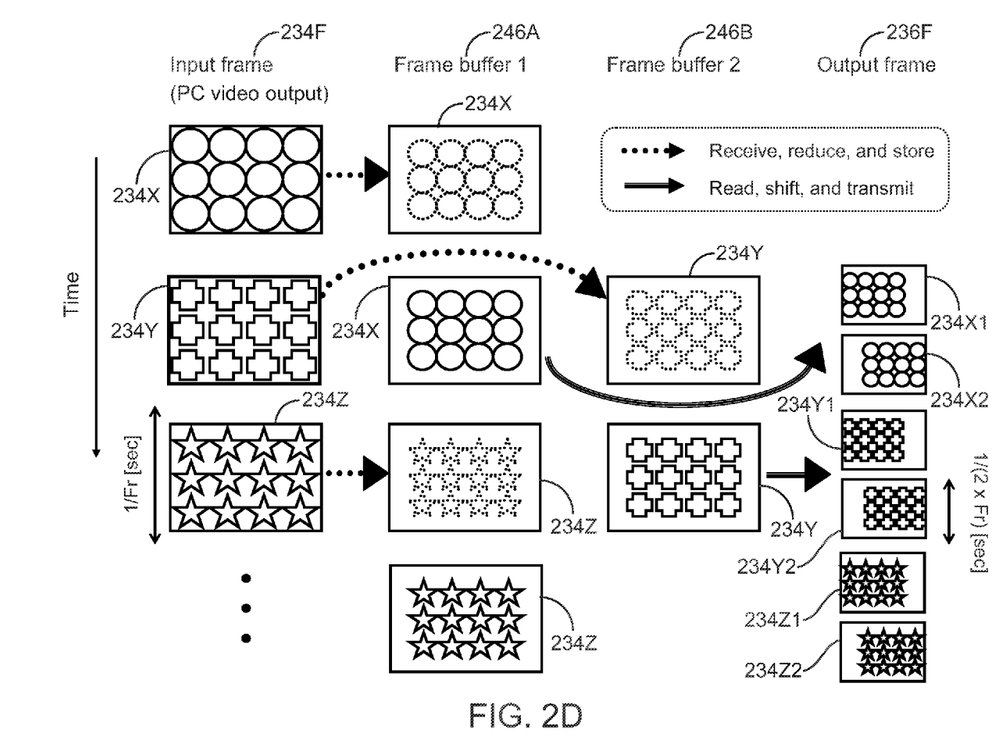
FIG. 2D shows an input frame, a first frame buffer, a second frame buffer, and an output frame of the system as in FIG. 2A, according to embodiments of the present invention.

FIG. 2D shows an input frame 234F, a first frame buffer 246A, a second frame buffer 246B, and an output frame 236F of the system as in FIG. 2A. Input frame 236F can be provided the PC video card output. Input frame 234F can be received, reduced and stored by one of first frame buffer 246A or second frame buffer 246B. In many embodiments, for example with computer games, movies, and computer graphics, the input frame can be received, and stored by one of first frame buffer 246A or second frame buffer 246B without frame size reduction to avoid cropping. In some embodiments, for example in some personal computers with Windows™ and/or Macintosh™, it may be helpful to reduce the input frame size and/or magnification of the images shown on the display so as to avoid cropping. Reduction of the frame can comprise a reduction in the magnification of an image in the frame such that the image and/or frame have a decreased size when shown on the display screen so as to avoid cropping of the shifted image. The reduction can occur before the image is split into left and right images, such that the magnification and size of the image shown to each eye is the same. A first input frame 234X can be received and reduced by the processor and stored in first frame buffer 246A. First input frame 234X can be read, shifted, and transmitted as output frame 234X1 and output frame 234X2. Output frame 234X1 can correspond to the frame seen with the left eye, and output frame 234X2 can correspond to the frame seen with the right eye. Output frame 234X1 can be shifted to the left and output frame 234X2 can be shifted to the right. A second input frame 234Y can be received and reduced by the processor and stored in second frame buffer 246B. Second input frame 234Y can be read, shifted, and transmitted as output frame 234Y1 and output frame 234Y2. Output frame 234Y1 can correspond to the frame seen with the left eye, and output frame 234Y2 can correspond to the frame seen with the right eye. A third input frame 234Z can be received and reduced by the processor and stored in first frame buffer 246A. Third input frame 234Z can be read, shifted, and transmitted as output frame 234Z1 and output frame 234Z2. Output frame 234Z1 can correspond to the frame seen with the left eye, and output frame 234Z2 can correspond to the frame seen with the right eye. Additional frames can be received, reduced, stored, read, shifted and transmitted accordingly.

In some embodiments, a rate of input frame 234F may be half a rate of output frame 236F. For an input frame rate (FR IN), in Hertz (Hz), the output frame rate (FR OUT) can be twice as much. Correspondingly, the period, or duration, of the output frames may be half the period of the input frames.

The electronic shift circuit can be used in many electronic devices. Displays that can benefit from embodiments of the present invention include known video game displays such as the Wii, the X-box and the Play Station commercially available from Nintendo, Microsoft and Sony, respectively. In some embodiments, the electronic shift circuit can be used with a television display.

Many adaptations can be made to the embodiments shown in FIGS. 2A to 2D. For example, the input frames may be cropped instead of reduced, and every other input frame can be dropped such that the period of the input frames matches the period of the output frames. In some embodiments, the shift distance may comprise a preselected default distance In many embodiments, the user can select the image shift distance based on user preference. For example, the user can find out the threshold distance which he/she can no longer see the target image as a single image. Then, the user can reduce the distance slightly to maximize relaxation.

Figure 3A:
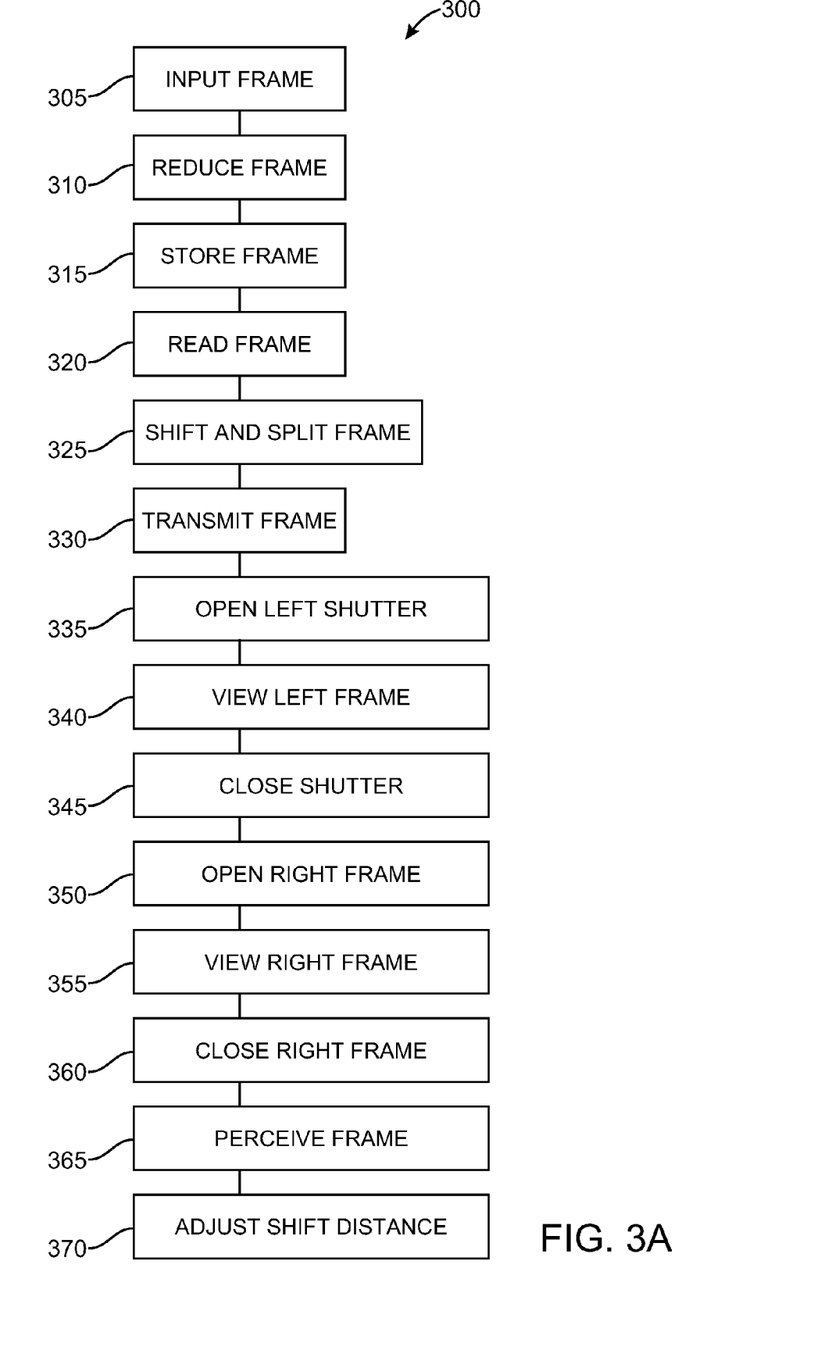
FIG. 3A shows a method to prevent and treat myopia and fatigue, according to embodiments of the present invention.

FIG. 3 shows a method 300 to prevent fatigue and treat myopia, according to embodiments of the present invention. Method 300 can be performed with shift circuitry comprising processor, as described above. A step 305 inputs a frame, for example a video frame comprising an image as described above. A step 310 reduces the frame to a suitable size such that the frame is not cropped when viewed. A step 315 stores the frame into a memory, for example a video memory buffer. A step 320 reads the frame. A step 325 shifts and splits the frame into frames that correspond to the left and right eyes, respectively. In some embodiments, the shift distance initially corresponds to a default distance, and the shift distance may be adjusted by the user in response to user perception and/or comfort. A step 330 transmits the frame to a display. A step 335 opens a left shutter such that the eye can view the left frame. A step 340 views the left frame with the left eye. A step 345 closes the left shutter. A step 250 opens the right shutter such that the right eye can view the right frame. A step 360 closes the right shutter.

In many embodiments, each of the frames is shifted by a user determined distance, for example a distance subjectively determined by the user to be comfortable. At step 365 the user perceives the shifted images, for example shift images on the display. A step 370 adjusts the shift distance. In many embodiments, the image shift distance can be adjusted for user comfort and the shift distance can be selected by the user in response to user perception of the images at the shift distance. The use can use an input device to adjust the selected distance. In some embodiments, the shift distance may progressively and/or incrementally increase until the user perceives two images instead of one image so as to establish a maximum shift distance, which is slightly less than the distance at which the user first perceives two images. In some embodiments, the user is provided with a software button, graphic display or the like to show the selected shift distance in relation to the established maximum shift distance. In some embodiments, the shift distance selected by the user in response to user perception and comfort may be less than the established maximum shift distance. Steps 305 to 370 can be repeated as long as is beneficial to provide relief to the eyes so as to avoid too much accommodation.

It should be appreciated that the specific steps illustrated in FIG. 3 provide a particular method of relaxing the eye, according to an embodiment of the present invention. Other sequences of steps may also be performed according to alternative embodiments. For example, alternative embodiments of the present invention may perform the steps outlined above in a different order. Moreover, the individual steps illustrated in FIG. 3 may include multiple sub-steps that may be performed in various sequences as appropriate to the individual step. Furthermore, additional steps may be added or removed depending on the particular applications. One of ordinary skill in the art would recognize many variations, modifications, and alternatives.

Experimental Testing

FIGS. 4A to 4D show experimental evidence of decreased response to a near stimulus with a shifted image, according to embodiments of the present invention. A visual stimulus was presented to test subject at a distance of one meter. One eye of the test subject was imaged with a digital movie camera calibrated such that pixels could be converted to distance. A prism was introduced in front of the left eye of the test subject to provide a virtual image of the test stimulus with a shifted location. The same eye was imaged with the digital camera. The pupil size was measured without the prism and with the prism. A distance along the eyelids was measured to compare the images taken with and without the prisms to ensure that the patient did not move so as to change the camera magnification.

Figure 4A:
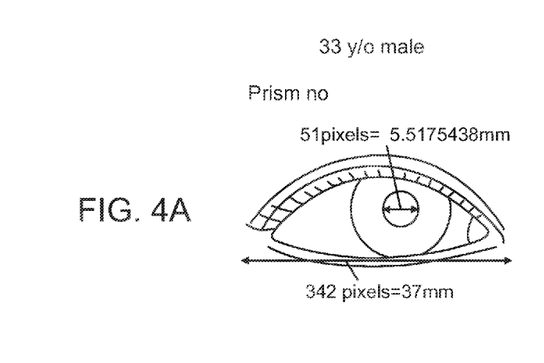
FIGS. 4A to 4D show experimental evidence of decreased response to a near stimulus with a shifted image, according to embodiments of the present invention.
Figure 4B:
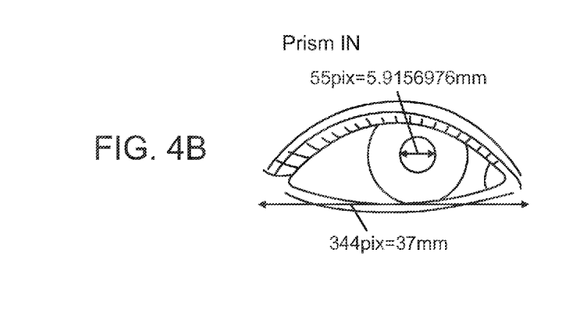

FIG. 4A shows the experimentally measured pupil size of 33 year old male measured with no prism. The shown pupil size is 5.5 mm. FIG. 4B shows the experimentally measure pupil size of the 33 year old male measured with the prism in place. The shown pupil size is 5.9 mm. Thus, the accommodation of the eye appeared to relax by shifting the image.

Figure 4C:
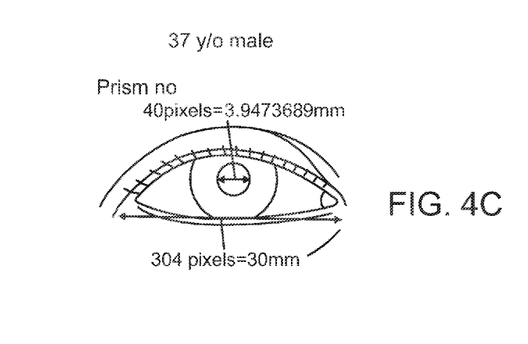
Figure 4D:
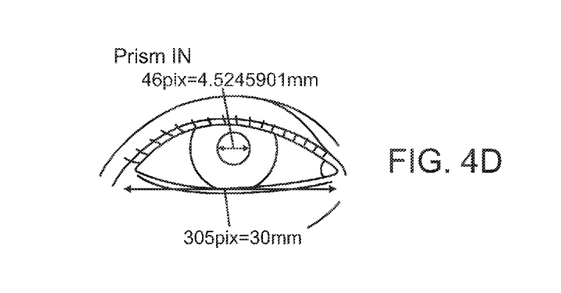

FIG. 4C shows the experimentally measured pupil size of 37 year old male measured with no prism. The shown pupil size is 3.9 mm. FIG. 4D shows the experimentally measure pupil size of the 37 year old male measured with the prism in place. The shown pupil size is 4.5 mm. Thus, the accommodation of the eye appeared to relax by shifting the image.

It is understood that other embodiments may fall within the spirit and scope of the invention. Therefore, the scope of the invention should be determined with reference to the appended claims along with their full scope of equivalents.

What is claimed is:

1. A method for relieving eye convergence while viewing an electronic image on a display, said method comprising:
shifting the electronic image horizontally on the display by a distance according to a time pattern; and
alternating left eye and right eye viewing of the display according to said time pattern;
wherein the distance is sufficient for each eye to view the image without substantial convergence.

2. A method as in claim 1, wherein the time pattern is invariant.

3. A method as in claim 2, wherein the images shift at a rate in the range from 30 Hz to 120 Hz.

4. A method as in claim 2, wherein the preselected distance is in the range from 0.1 cm to 5 cm.

5. A method as in claim 1, wherein alternating left eye and right eye vision comprises alternately opening and shutting a shutter worn over each eye.

6. A method as in claim 5, wherein opening and shutting comprises energizing and de-energizing liquid crystal shutters.

7. A method as in claim 5, wherein opening and shutting comprises opening and closing mechanical shutters.

8. A method as in claim 1, wherein the image shift distance comprises a preselected distance.

9. A method as in claim 1, wherein the image shift distance corresponds to a distance selected by the user.

10. A method as in claim 9, wherein the distance selected by the user is perceived by the user and selected in response to user comfort.

11. A method as in claim 9, wherein the image shift distance is incrementally increased to a maximum distance for which the user perceives the image as a single image.

12. A method as in claim 1, wherein the image is shifted to the left when viewed with left eye of the user and the image is shifted to the right when viewed with a right eye of the user.

13. A method as in claim 1, wherein a magnification of the image is decreased by an amount for viewing with each eye, and the amount is the same for each eye.

14. A method as in claim 1, wherein a magnification of the image is decreased by for viewing with each eye such that a size of the image on the display is reduced and the image is not cropped when shifted for viewing with each eye on the display.

15. A system for relieving eye convergence while viewing an electronic image on a display, said system comprising:
electronic circuitry configured to receive an electronic image and generate an output comprising a series of frames of the image, the frames alternately right shifted and left shifted on the display by a distance according to a time pattern, the distance sufficient for each eye to view the image without substantial convergence; and left eye and right eye shutters which are configured to alternately open and close according to the time pattern.

16. A system as in claim 15, further comprising a display which is connected to receive the output of the electronic circuitry.

17. A system as in claim 16, further comprising a source connected to feed the electronic image to the electronic circuitry.

18. A system as in claim 15, wherein the electronic circuitry produces a timing signal which is coupled to the left eye and right eye shutters.

19. A system as in claim 18, wherein the timing signal is coupled by a wire from the electronic circuitry to the left eye and right eye shutters.

20. A system as in claim 18, wherein the timing signal is wirelessly coupled from the electronic circuitry to the left eye and right eye shutters.

21. A system as in claim 15, wherein the time pattern is invariant.

22. A system as in claim 21, wherein the electronic circuitry is configured to shift the images at a rate in a range from 30 Hz to 120 Hz.

23. A system as in claim 21, wherein the image shift distance is in a range from 0.1 cm to 5 cm.

24. A system as in claim 15, wherein the image shift distance is user selectable with an input from a device, and the electronic circuitry is configured to adjust the preselected distance in response to the input.

25. A system as in claim 24, wherein the electronic circuitry is configured to display the alternately right shifted and left shifted frames on the display such that the user can select the distance.

26. A system as in claim 24, wherein the electronic circuitry is configured to increase incrementally the distance to a maximum distance for which the user perceives the image as a single image.

27. A system as in claim 15, wherein the electronic circuitry is configured to open and shut a shutter worn over each eye so as to alternate left eye and right eye vision.

28. A system as in claim 27, wherein the left eye and right eye shutters comprise liquid crystal shutters configured to open and close in response to a timing signal from the electronic circuitry.

29. A system as in claim 27, wherein the left eye and right eye shutters comprise mechanical shutters configured to open and close in response to a timing signal from the electronic circuitry.

30. A system as in claim 15, further comprising a frame configured to be worn by a user, wherein the left and right eye shutters are mounted on the frame.

31. A system as in claim 30, further comprising a left lens and a right lens, each connected to the frame to correct vision of the user.

32. A system as in claim 30, wherein the frames and shutters are configured for use with lenses that correct vision of the user.

33. A system as in claim 32, wherein the lenses correct at least one of a nearsightedness, a farsightedness, an astigmatism or a pseudomyopia of the user.

34. A system as in claim 32, wherein the lenses comprise reading glasses.

* * * * *